US006228058B1

United States Patent
Dennis et al.

(10) Patent No.: US 6,228,058 B1
(45) Date of Patent: May 8, 2001

(54) SLEEVE TROCAR WITH PENETRATION INDICATOR

(75) Inventors: William G. Dennis; Michael E. Prosek, both of Jacksonville, FL (US)

(73) Assignee: Core Dynamics, Inc., Jacksonville, FL (US)

( * ) Notice: Subject to any disclaimer, the term of this patent is extended or adjusted under 35 U.S.C. 154(b) by 0 days.

(21) Appl. No.: 09/209,225

(22) Filed: Dec. 10, 1998

Related U.S. Application Data

(63) Continuation-in-part of application No. 08/832,294, filed on Apr. 3, 1997, now Pat. No. 5,853,392.

(51) Int. Cl.$^7$ .................................................. A61M 5/178
(52) U.S. Cl. .......................................................... 604/164.01
(58) Field of Search ................................. 604/164, 158, 604/118, 51, 48, 111, 160, 166, 168, 264, 272, 900; 606/167, 181, 185

(56) References Cited

U.S. PATENT DOCUMENTS

| | | | |
|---|---|---|---|
| 5,057,082 | 10/1991 | Burchette | 604/164 |
| 5,114,407 | 5/1992 | Burbank | 604/164 |
| 5,224,951 | 7/1993 | Freitas | 606/172 |
| 5,224,952 | 7/1993 | Deniega et al. | 606/184 |
| 5,226,426 | 7/1993 | Yoon | 128/753 |
| 5,261,891 | 11/1993 | Brinkerhoff et al. | 604/164 |
| 5,290,243 | 3/1994 | Chodorow et al. | 604/165 |
| 5,300,036 | 4/1994 | Mueller et al. | 604/167 |
| 5,330,432 | 7/1994 | Yoon | 604/164 |
| 5,336,176 | 8/1994 | Yoon | 604/51 |
| 5,342,382 | 8/1994 | Brinkerhoff et al. | 606/184 |
| 5,346,459 | 9/1994 | Allen | 606/185 |
| 5,364,372 | 11/1994 | Danks et al. | 604/264 |
| 5,368,607 | 11/1994 | Freitas | 606/172 |
| 5,401,247 | 3/1995 | Yoon | 604/165 |
| 5,405,328 | 4/1995 | Vidal et al. | 604/158 |
| 5,411,515 | 5/1995 | Haber et al. | 606/184 |
| 5,423,760 | 6/1995 | Yoon | 604/165 |
| 5,423,770 | 6/1995 | Yoon | 604/281 |
| 5,431,635 | 7/1995 | Yoon | 604/165 |
| 5,445,617 | 8/1995 | Yoon | 604/165 |
| 5,466,224 | 11/1995 | Yoon | 604/165 |
| 5,474,539 | 12/1995 | Costa et al. | 604/164 |
| 5,478,317 | 12/1995 | Yoon | 604/165 |
| 5,486,190 | 1/1996 | Green | 606/184 |
| 5,496,289 | 3/1996 | Wenstrom | 604/264 |
| 5,522,833 | 6/1996 | Stephens et al. | 606/185 |
| 5,533,977 | * 7/1996 | Metcalf et al. | 604/164 |
| 5,534,009 | 7/1996 | Lander | 606/185 |
| 5,549,564 | 8/1996 | Yoon | 604/165 |
| 5,569,288 | 10/1996 | Yoon | 606/185 |
| 5,569,289 | 10/1996 | Yoon | 606/185 |
| 5,569,293 | 10/1996 | Yoon | 606/185 |
| 5,571,134 | 11/1996 | Yoon | 606/185 |
| 5,573,511 | * 11/1996 | Yoon | 604/164 |
| 5,573,545 | 11/1996 | Yoon | 606/185 |
| 5,575,804 | 11/1996 | Yoon | 606/185 |
| 5,584,848 | 12/1996 | Yoon | 606/185 |
| 5,584,849 | 12/1996 | Yoon | 606/185 |
| 5,591,189 | 1/1997 | Yoon | 606/185 |
| 5,591,190 | 1/1997 | Yoon | 606/185 |

(List continued on next page.)

Primary Examiner—Sharon Kennedy
Assistant Examiner—Ann Y. Lam
(74) Attorney, Agent, or Firm—McGuireWoods LLP

(57) ABSTRACT

A sleeve trocar for piercing tissue to provide a conduit to an internal body cavity insufflated by gas includes a generally tubular sleeve member having a cutting edge and a passageway therethrough. An obturator assembly is telescopically disposed within the sleeve member with the obturator assembly having a moveable portion and a stationary portion, each obturator portion having a blunt face projecting beyond the cutting edge. The present invention also includes a penetration indicator assembly which provides an audible sound upon breach of a body cavity wall.

54 Claims, 7 Drawing Sheets

U.S. PATENT DOCUMENTS

| | | | |
|---|---|---|---|
| 5,591,193 | 1/1997 | Yoon | 606/185 |
| 5,690,663 * | 11/1997 | Stephens | 606/185 |
| 5,730,755 | 3/1998 | Yoon | 606/185 |
| 5,776,112 | 7/1998 | Stephens et al. | 604/264 |
| 5,776,156 | 7/1998 | Shikhman | 606/170 |
| 5,807,338 | 9/1998 | Smith et al. | 604/164 |
| 5,807,402 | 9/1998 | Yoon | 606/185 |
| 5,810,866 | 9/1998 | Yoon | 606/185 |
| 5,817,061 | 10/1998 | Goodwin et al. | 604/164 |
| 5,824,002 | 10/1998 | Gentelia et al. | 604/164 |

* cited by examiner

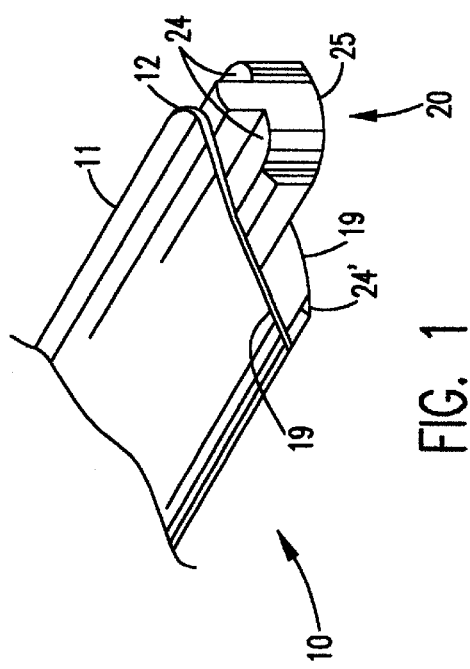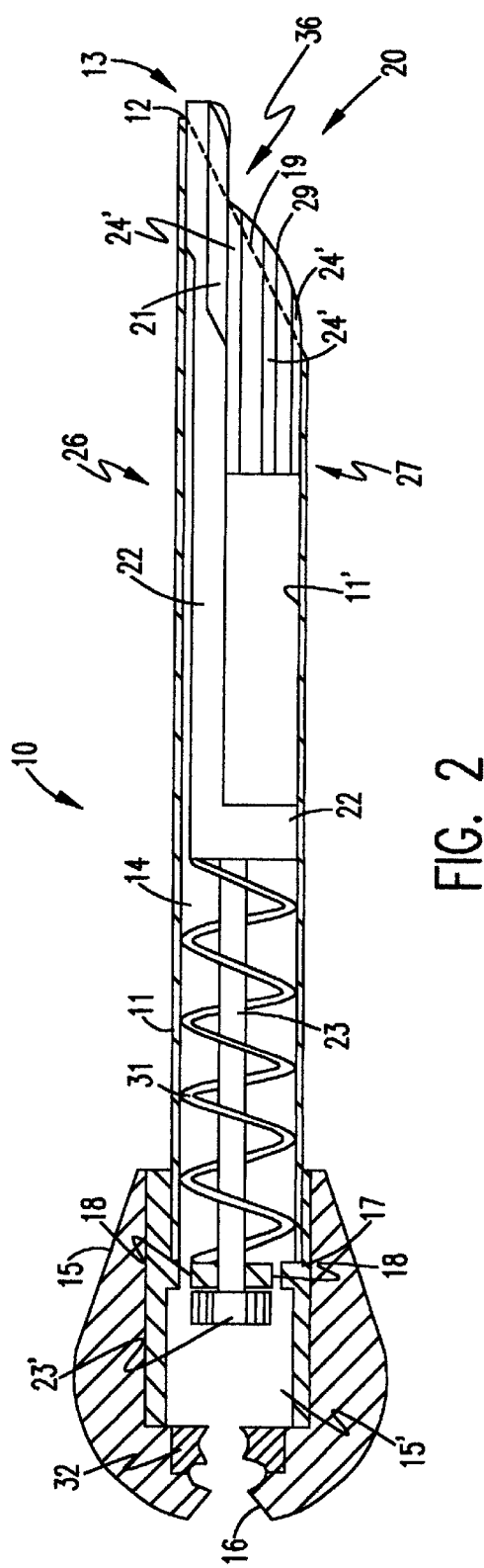

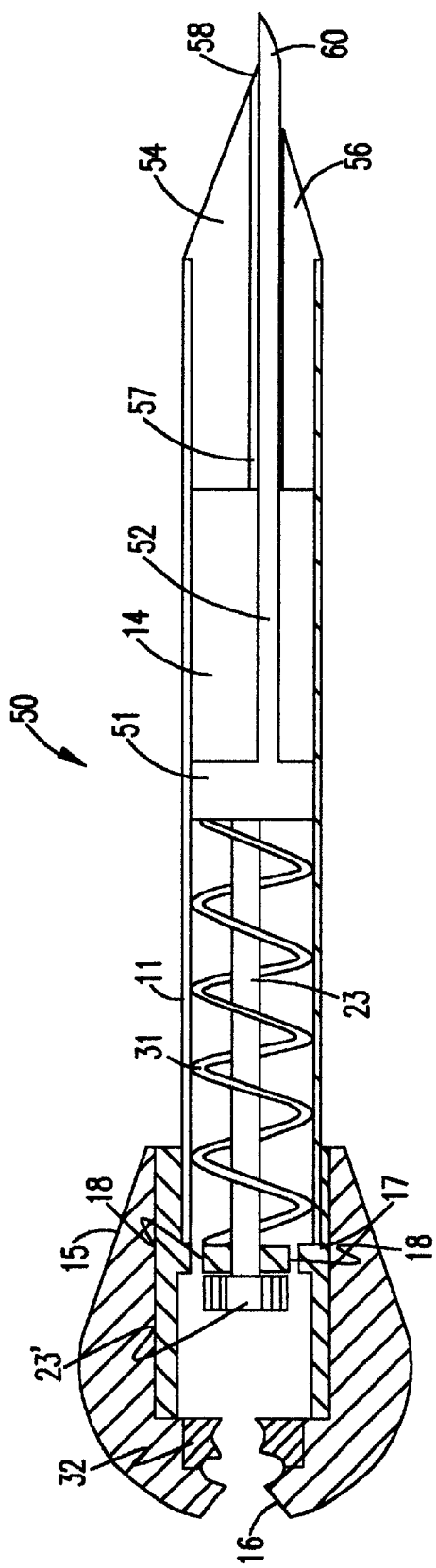
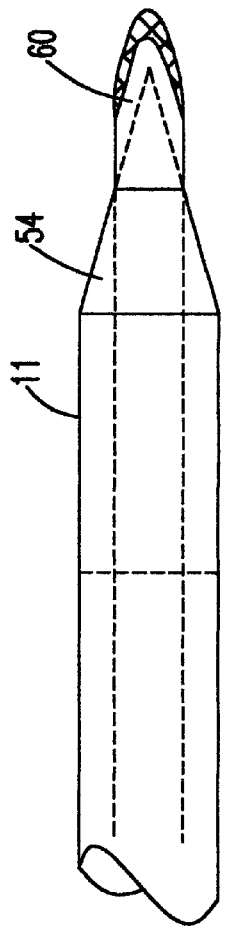
FIG. 10
FIG. 11

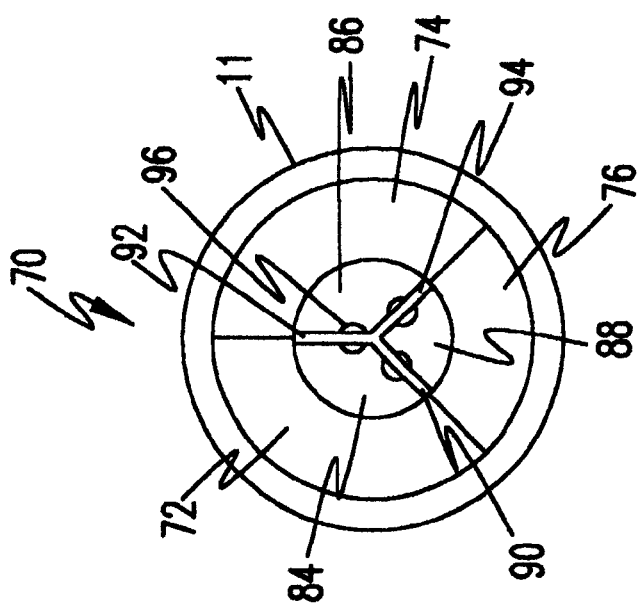
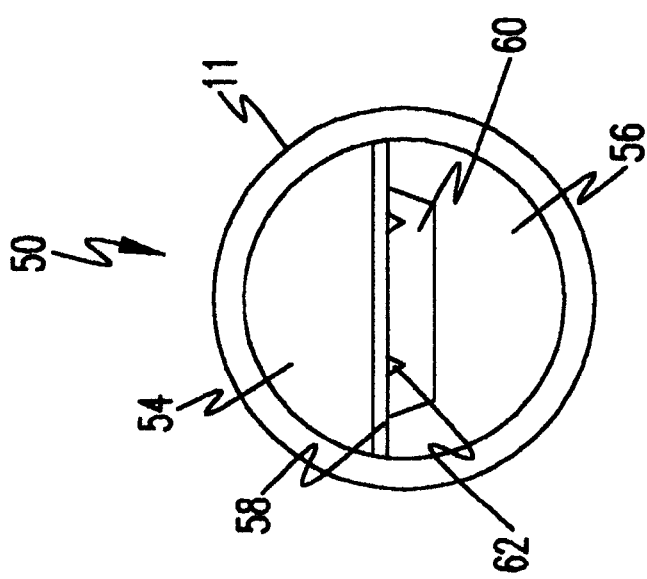

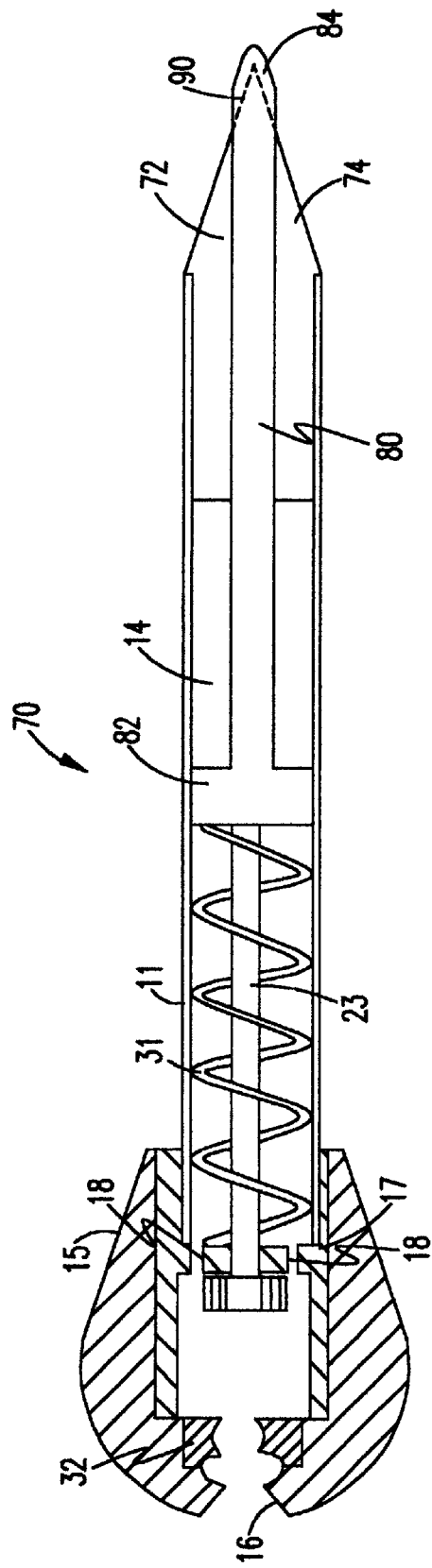
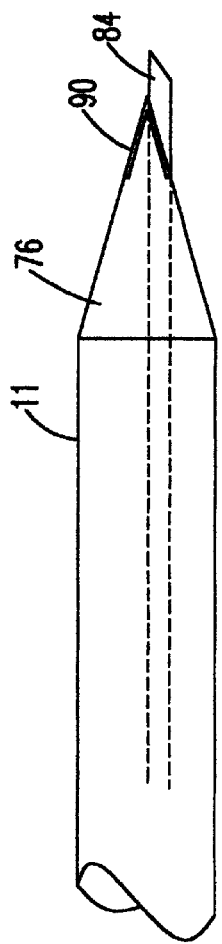
FIG. 13
FIG. 14

SLEEVE TROCAR WITH PENETRATION INDICATOR

This is a continuation-in-part of Ser. No. 08/832,294, filed Apr. 3, 1997, U.S. Pat. No. 5,853,392, issued Dec. 29, 1998.

BACKGROUND OF THE INVENTION

The present invention relates broadly to body cavity piercing devices used in surgery to provide access to internal cavities through small puncture sites rather than large incisions. More particularly, the present invention is directed to such a body cavity piercing device, known as a trocar, having a multi-portion obturator, or multiple obturator portions.

A standard trocar is typically a pointed rod, usually formed from metal, which is designed to be contained within a blunt-tipped sleeve known as a cannula. The tip of the trocar is typically needle-like with a beveled piercing tip having sharp edges.

A tissue puncture is manually conducted with the combination trocar and cannula, and then the trocar is removed from the cannula The cannula is left in place to provide an access conduit to the internal body cavity. According to one of two typical trocar designs, a retractable sleeve is positioned around the trocar, with the sleeve being biased such that it slides back on contact with the outer walls of the body cavity covering to expose the tip of the trocar during insertion, but is advanced forwardly to cover the sharp point of the trocar once the internal cavity has been breached.

Another style of trocar is similar in design to a Verress needle, which consists of a sharp tubular needle with an internal blunt obturator provided with a passageway for fluid, the internal obturator being spring biased so that it is forced into the body of the needle during piercing or puncture. Throughout the present application, the terms piercing and puncturing are used interchangeably. The tubular needle itself pierces the tissue, while the obturator blocks the interior of the needle to prevent tissue from entering into the needle. This type of trocar, which is also used in combination with a cannula, has a sharp tubular member or sleeve containing a retractable obturator, with the obturator being spring biased so that the tissue will push it some small distance into the sleeve during the puncture or piercing event. When the tip of the trocar reaches the internal cavity, which is usually inflated with a gas in a procedure known as insufflation, to provide an enlarged cavity, the biasing spring pushes the obturator forward past the sharp tip of the sleeve to prevent accidental puncturing or cutting of internal organs.

It is sometimes difficult for a surgeon to ascertain when the internal cavity wall has been breached by the trocar. Typically, the only indication provided by a standard trocar is a reduction in the amount of resistance felt by the surgeon, with a vibration or sound caused by the forward movement of the spring biased sleeve or obturator once the trocar has entered the internal cavity. Various devices have been developed to provide a more positive indication of when the cavity wall has been breached. These devices typically utilize visual or audible signals.

Other problems with conventional trocar assemblies include the capture of tissue intermediate the obturator and the piercing sleeve wall when the obturator is retracted or pushed back by the body cavity wall. Since the tip is beveled, the initial piercing and cutting is performed by the forwardmost extent of the blade formed on the beveled edge of the sleeve. Once the initial opening is formed, further insertion of the trocar generally forms an aperture in the body cavity wall absent any meaningful cutting action from the remainder of the beveled edge of the trocar sleeve. Therefore, the cut at the trailing edge of the beveled tip may not be as smoothly formed as the initial cut and retraction of the obturator can capture tissue intermediate the obturator and the sleeve.

SUMMARY OF THE INVENTION

It is accordingly an object of the present invention to provide a sleeve trocar which reduces the capture and withdrawal of tissue during obturator retraction.

It is another object to the present invention to provide such a trocar that provides an audible signal responsive to gas release when entry into the body cavity has occurred.

It is another object to the present intention to provide such a trocar that improves the speed at which the obturator projects ahead of the tip upon breach of the body cavity wall.

To those ends, a sleeve trocar for piercing tissue to provide a conduit to an internal body cavity insufflated by gas includes a sleeve member having a generally tubular wall member defining a bore therethrough, and a cutting edge. The trocar also includes an obturator assembly telescopically disposed within the sleeve member, the obturator assembly including at least one moveable obturator portion having a generally blunt tip. The at least one moveable obturator portion is moveable between a first position wherein the generally blunt tip projects beyond the wall member and a second position wherein the generally blunt tip is disposed interiorly of at least a portion of the cutting edge. The obturator assembly further includes at least one stationary obturator portion having a face member, the at least one stationary obturator portion being fixed relative to the sleeve member with the face member projecting beyond a portion of the wall member. An assembly for biasing the at least one moveable obturator portion into the first position is also included. It is preferred that the sleeve member include a cutting edge with a sharp piercing tip formed thereon and the moveable obturator portion projects beyond the piercing tip in the first position.

Preferably, the at least one stationary obturator portion includes a plug member fixedly disposed within the sleeve member with the face member being formed on one end of the plug member and projecting beyond an end portion of the wall member. The face member preferably includes a smoothly contoured surface for smooth separation of tissue during piercing for enhanced ease of entry of the trocar into the body cavity.

The trocar preferably further includes a penetration indication assembly including a penetration indicator operatively associated with the sleeve member and at least one passageway formed in the obturator assembly in fluid communication with the penetration indicator to allow gas to flow from a pierced body cavity through the at least one passageway to actuate the penetration indicator. It is preferred that the penetration indicator produce an audible signal responsive to gas from the body cavity passing therethrough to thereby indicate that a body cavity wall has been breached.

It is further preferred that the trocar include a handle formed on one end of the sleeve member and having a bore extending therethrough to form the penetration indicator, the bore being in fluid communication with the at least one passageway and configured to produce an audible signal responsive to gas from the body cavity passing therethrough thereby indicating that a body cavity wall has been breached.

Preferably, the penetration indication assembly includes a plurality of passageways formed about a periphery of the at least one moveable obturator portion to form peripheral passageways, the peripheral passageway being formed by a combination of the tubular wall of the sleeve member and walls formed in the periphery of the at least one moveable obturator portion. A plurality of passageways may also be formed about a periphery of the at least one stationary obturator portion to form peripheral passageways with the peripheral passageways being formed by a combination of the tubular wall of the sleeve member and walls formed in the periphery of the at least one stationary obturator portion. Further, a plurality of passageways may be formed about respective peripheries of the at least one moveable obturator portion and the at least one stationary obturator portion to form peripheral passageways, the peripheral passageways being formed by a combination of the tubular wall of the sleeve member and walls formed in the respective peripheries of the at least one moveable obturator portion and the at least one stationary obturator portion.

The plurality of passageways may also be formed as throughbores in the face member to extend through the face member and the stationary obturator portion in fluid communication with the bore in the sleeve member and the bore in the handle. Preferably, the assembly for biasing the at least one moveable obturator portion into the first position includes a spring disposed within the tubular sleeve member, the spring being fixed at one end to the at least one moveable obturator portion with the other end fixed within the sleeve member.

According to one preferred embodiment of the present invention, a sleeve trocar for piercing tissue to provide a conduit to an internal body cavity insufflated by gas includes a sleeve member having a generally tubular wall member defining a bore through the sleeve member, a first end portion formed with a beveled cutting edge having a piercing tip formed thereon and defining an aperture region for forming and defining an aperture in body cavity walls and an opposing end portion. The sleeve trocar also includes an obturator assembly telescopically disposed within the sleeve member, the obturator assembly including an obturator head having a generally blunt tip, the obturator head being moveable between the first position wherein the generally blunt tip projects beyond the piercing tip and a second position wherein the generally blunt tip is disposed within the bore, the obturator head being sized to occupy a predetermined portion of the aperture region leaving a remainder of the aperture region. An arrangement for biasing the obturator head into the first position is also provided. The trocar further includes an obturation face member fixed relative to the sleeve member with a portion of the obturation face member projecting beyond a portion of the cutting edge, the obturation face member being sized to occupy the remainder of the aperture region.

Preferably, the obturator head is sized to occupy less than half of the aperture region. Further, it is preferred that the obturation face member include a plug member fixedly disposed within the sleeve member with a face projection being formed on one end of the plug member and sized to project beyond a portion of the beveled cutting edge. It is further preferred that the face projection include a smoothly contoured surface for smooth separation of tissue for enhanced ease of entry of the trocar into the body cavity. It is further preferred that the obturation face member be formed integrally with the sleeve member with a face projection sized to project beyond a portion of the beveled cutting edge.

It is further preferred that the sleeve trocar according to this preferred embodiment include a penetration indication assembly including a penetration indicator operatively associated with the sleeve member and at least one passageway formed in the obturator head in fluid communication with the penetration indicator to allow gas to flow from a pierced body cavity through the at least one passageway to actuate the penetration indicator. Preferably, the penetration indicator produces an audible signal responsive to gas from the body cavity passing therethrough to thereby indicate that a body cavity wall has been breached. Further, it is preferred that a handle is formed on the opposing end of the sleeve member and the penetration indicator is formed as a bore extending through the handle in fluid communication with the at least one passageway and configured to produce an audible signal responsive to gas from the body cavity passing therethrough thereby indicating that a body cavity wall has been breached.

The penetration indication assembly preferably includes a plurality of passageways formed around a periphery of the obturator head to form peripheral passageways, the peripheral passageways being formed by a combination of the tubular wall of the sleeve member and walls formed in the periphery of the obturator head. Further, the penetration indication assembly may include a plurality of passageways formed about a periphery of the obturation face member to form peripheral passageways, the peripheral passageways being formed by a combination of the tubular wall of the sleeve member and walls formed in the periphery of the obturation face member. Further, the penetration assembly may include a plurality of passageways formed about respective peripheries of the obturator head and the obturation face member to form peripheral passageways, the peripheral passageways being formed by a combination of the tubular wall of the sleeve member and walls formed in the respective peripheries of the obturator head and the obturation face member. These passageways may be formed as throughbores in the face member to extend through the face member and the stationary obturator portion in fluid communication with the bore formed in the sleeve member and the bore formed in the handle.

The arrangement for biasing the obturator head into the first position preferably includes a spring disposed within the tubular sleeve member, the spring being fixed in one end to the obturator head with the other end fixed within the sleeve member for biasing the obturator head outwardly beyond the piercing tip.

According to another preferred embodiment of the present invention, the obturator assembly includes a conical stationary obturator portion fixed in the sleeve member and projecting outwardly therefrom, and at least one moveable obturator portion having a generally blunt tip, the at least one moveable obturator portion being moveable between a first position wherein said generally blunt tip projects beyond said stationary portion and a second position wherein said generally blunt tip is disposed within said conical obturator head, the conical stationary obturator portion being formed from at least two obturator members in abutment with one another, extending a predetermined distance into the bore formed in the sleeve member and having an obturator passage formed therebetween with the moveable obturator portion being disposed in the obturator passage for movement between the first and second positions. It is preferred that the trocar further include a cutting edge formed on at least one of the stationary obturator members adjacent the passage.

This embodiment preferably includes a penetration indication assembly including a penetration indicator operatively associated with the sleeve member and at least one passageway formed in the obturator assembly in fluid communication with the penetration indicator to allow gas to flow from a pierced body cavity through the at least one passageway to actuate the penetration indicator. It is preferred that the moveable obturator portion include the at least one passageway formed therein as at least one throughbore formed in fluid communication with the penetration indicator to allow gas to flow from a pierced body cavity through the at least one throughbore to actuate the penetration indicator.

According to another preferred embodiment of the present invention, the obturator assembly includes a cutting edge, a conical stationary obturator portion fixed in the sleeve member and projecting outwardly therefrom with the conical stationary obturator portion being formed from at least three obturator members in abutment with one another, extending a predetermined distance into the bore and having three obturator passages formed therebetween. The moveable obturator portion is formed as three moveable obturator members disposed in respective obturator passages for movement between the first position and second position wherein the moveable obturator portion is disposed interiorly of the cutting edge. Preferably, the cutting edge is formed on at least one of the three obturator members adjacent the moveable obturator portion.

The trocar according to this preferred embodiment further preferably includes a penetration indication assembly including a penetration indicator operatively associated with the sleeve member and at least one passageway formed in the obturator assembly in fluid assembly with the penetration indicator to allow gas to flow from a pierced body cavity through the at least one passageway to actuate the penetration indicator. Preferably, the moveable obturator portion includes at least one passageway formed therein as at least one throughbore formed in fluid communication with the penetration indicator to allow gas to flow from a pierced body cavity through the at least one throughbore to actuate the penetration indicator.

By the above, the present invention provides an obturator with enhanced performance characteristics that will provide an audible signal when the body cavity wall is breached and will reduce tissue collection intermediate the obturator and the sleeve member.

BRIEF DESCRIPTION OF THE DRAWINGS

FIG. 1 is a partial perspective view of the piercing end of a sleeve trocar according to the preferred embodiment of the present invention;

FIG. 2 is a cross-sectional view showing the sleeve trocar with the obturator exposed;

FIG. 10 is a cross sectional view of the sleeve trocar according to another preferred embodiment thereof;

FIG. 11 is a top view of a portion of the trocar illustrated in FIG. 10;

FIG. 12 is an end view of the trocar illustrated in FIG. 10;

FIG. 13 is a cross sectional view of the sleeve trocar according to another preferred embodiment of the present invention;

FIG. 14 is a top view of a portion of the sleeve trocar illustrated in FIG. 13; and FIG. 15 is an end view of the sleeve trocar illustrated in FIG. 13.

DESCRIPTION OF THE PREFERRED EMBODIMENTS

Figure 5:
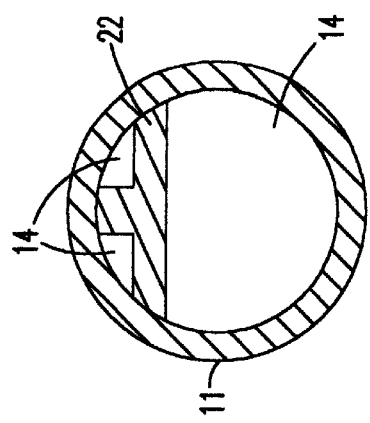
FIG. 5 is cross-sectional view showing the obturator body and the sleeve member taken along line V—V FIG. 2.

Turning now to the drawings, and more particularly to FIG. 1, a sleeve trocar according to the preferred embodiment of the present invention is illustrated generally at 10. A trocar is a puncturing instrument used in surgery to provide a relatively small access opening through outer tissue and muscle layers into an internal body cavity. The cavity is typically insufflated by the introduction of gas prior to use of the trocar. The trocar is coaxially aligned with the cannula such that after the puncturing event the cannula is left in place and the trocar is removed to provide an open conduit into the body cavity. A sleeve trocar typically includes a hollow sleeve member having a sharpened end or tip which contains a coaxially mounted, spring biased obturator. The obturator is typically moveable to extend beyond the piercing tip of the sleeve member unless forced into the sleeve member when the body tissue is first encountered during a piercing or puncturing step. When the body cavity is breached, the spring biasing member extends the blunt end of the obturator past the piercing end to prevent accidental puncturing or cutting of the internal organs by sharpened end.

With reference to FIGS. 1 and 2, a trocar according to the present invention 10 includes an elongate, sleeve member 11 having a tubular wall 11', a beveled, needle-like end portion 13 with the beveled end portion 13 defining in a cutting edge 19. The edge 19 is typically sharpened throughout its circumference for effective piercing of body cavity wall tissue. A handle 15 is disposed at the opposing end of the sleeve member 11 with the handle 15 being a bulb-like configuration for ease of use by a surgeon or other user. The sleeve member 11 is substantially hollow to define an interior bore 14 extending therethrough. A venting aperture 16 is formed in the end of the handle 15 in fluid communication with the interior bore 14 to allow any gasses flowing in the beveled end portion 13 to flow through the interior bore 14 and out the ventilation aperture 16 in a manner that will be described in greater detail hereinafter.

An obturator assembly 20 is disposed telescopically within the sleeve member 11. The obturator assembly includes at least one movable obturator portion 26 which is slideably mounted within the sleeve member 11. At least one stationary obturator portion 27 is fixed in the sleeve member 11 with the moveable obturator portion 26 slideably disposed intermediate the stationary obturator portion 27 and inner walls of the sleeve member 11.

The first obturator portion 26 is formed with a generally elongate obturator body 22 terminating in a blunt, curved tip 25, the blunt tip 25 being depicted in FIG. 1. The blunt tip 25 is formed on an obturator head portion 21 projecting outwardly from the obturator body 22. A thrust member 22' is formed integrally with the first obturator body 22 to extend perpendicularly away therefrom at an end of the first obturator body opposite the blunt tip 25. The thrust member 22' extends across the internal bore 14 of the sleeve member 11. An obturator shaft 23 is fixed to the thrust member 22' and extends outwardly therefrom in a direction away from the obturator body 22. A generally H-shaped insert member 17 is positioned within the sleeve member 11 with the shaft 23 extending therethrough. Flow passageways 18 are formed in the insert member 17 to allow insufflation gas to pass beyond the insert member 17, through the handle 15 and outwardly through the venting aperture 16. A cap 23' is attached to the end of the shaft 23 on the outer side of the insert member 17 to limit motion of the first obturator portion 26 such that the blunt tip 25 is allowed to project a predetermined distance beyond the piercing tip 12. A cavity 15' is formed in the handle 15 to allow the cap 23' along with the shaft 23 to move in a reciprocatory manner therethrough to define the limits of motion for the first obturator portion 26.

The first obturator portion 26 is biased so that the blunt tip 25 naturally extends beyond the tubular wall 11' at the piercing tip 12 to protect the piercing tip 12 and those who would come in contact with the piercing tip 12. Biasing is accomplished using a spring 31 that extends between the thrust member 22' and the insert member 17. The spring is maintained under some compression to provide the biasing force for the first obturator portion 26. Under a static condition, the cap 23' is in abutment with the insert member 17 with the blunt tip 25 projecting beyond the piercing tip 12. This condition may be opposed by pushing the blunt tip 25 and, thereby, the first obturator portion 26 against the spring 31 which will cause the cap 23' to move away from the insert member 17 within the handle cavity 15'.

Figure 4:
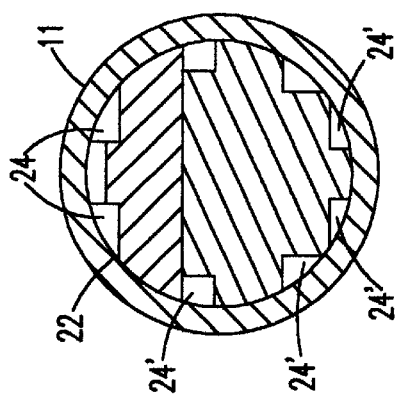
FIG. 4 is a cross-sectional view showing the obturator head in the sleeve member taken along line IV—IV of FIG. 2.
Figure 6:
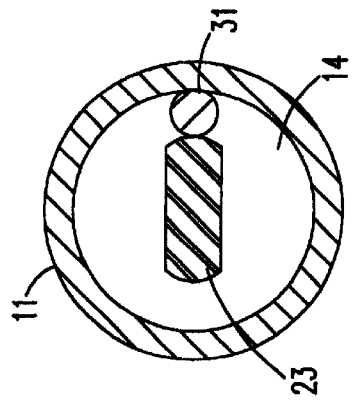
FIG. 6 is a cross-sectional view showing the obturator shaft in the sleeve member taken along line VI—VI of FIG. 2.

As seen in FIG. 1, the obturator head 21 includes two groove-like passageways 24 formed in the periphery thereof. These first obturator peripheral passageways 24 are best seen in FIG. 1 and are provided to allow gas to flow from an insufflated body cavity into the interior bore 14 of the shaft member 11. Such gas passageways are thusly defined by the first obturator passageways 24 and the interior walls of the sleeve member 11. The peripheral passageways 24 as shown in FIGS. 1 and 4 are rectilinear in cross-section, but they may be of any cross-sectional configuration. The peripheral passageways 24 extend the full length of the obturator head 21 and open into the interior bore 14. The passageways may also expand or contract dimensionally over their length.

Preferably, the obturator body 22 is configured with a smaller cross-sectional area than the obturator head 21 and, most preferably, has a relatively minimal cross-sectional area in order to allow for unimpeded flow within the sleeve member 11 as illustrated in FIG. 5 with the obturator body 22 being configured in an inverted T-configuration. The obturator shaft 23 and spring member 31 are likewise preferably kept small in total volume, so that gas flow from the internal cavity through the peripheral passageways 24 and sleeve interior 14 to the flow apertures 18 is unimpeded. By positioning the passageways 24 around the exterior periphery of the first obturator head 21 and abutting the interior wall of the sleeve member 11, the likelihood of the passageways 24 being blocked by tissue during the puncturing or piercing step is reduced.

Figure 3:
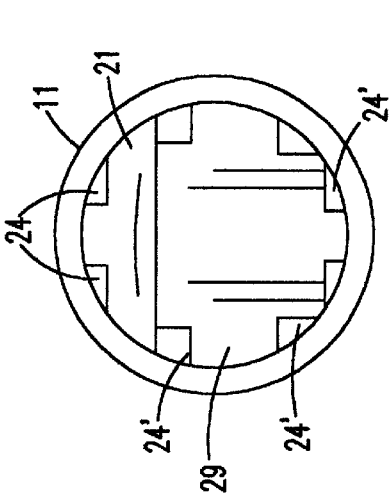
FIG. 3 as an end view of the piercing end of the device.

Further reduction of tissue acquisition by the obturator assembly 20 is provided in the form of the stationary obturator portion 27. The stationary obturator portion 27 may be formed in several ways. The preferred manner is illustrated in FIG. 2 and includes a plug member 28 having a smoothly contoured face 29 formed thereon to extend beyond the cutting edge 19 of the sleeve member 11. The cutting edge 19 is not as pronounced at the rearwardmost portion of the beveled end. Known as an "anticoring heel," this area experiences reduced tissue capture, a feature that is enhanced by the present invention. The cutting edge 19 may be configured to define an aperture region which, when in use, defines the aperture formed in the body cavity wall. The present invention reduces the size of the cut, providing a reduced trocar wound defect. The aperture region is occupied by the moveable obturator portion 26 and the stationary obturator portion 27. The moveable obturator portion 26 occupies a predetermined portion of the aperture region 36 and preferably less than half of the aperture region 36. The remainder of the aperture region 36 is occupied by the plug member 28 as seen in FIG. 2. The face 29 of the plug member 28 is smoothly contoured and is devoid of any beveling that is commonplace among existing trocars. This contour acts to further reduce the trocar wound defect. The face 29 projects beyond the cutting edge 19 within the aperture region 36 to smoothly direct tissue away from the obturator during the puncturing or piercing step. Optionally, passageways 24' may be formed in the outer surface of the plug member 28 to enhance the ability of the present trocar 10 to pass gas from the internal body cavity therethrough, as seen in FIGS. 3 and 7.

The present invention also provides a penetration indication assembly which includes the aforesaid passageways 24, 24' and a penetration indicator 32 formed in the end portion of the handle 15. The penetration indicator 32 is a tuned vent which will provide an audible signal when gas or air is directed therethrough under pressure. Operation of the penetration indicator 32 will be explained in greater detail hereinafter.

Figure 7:
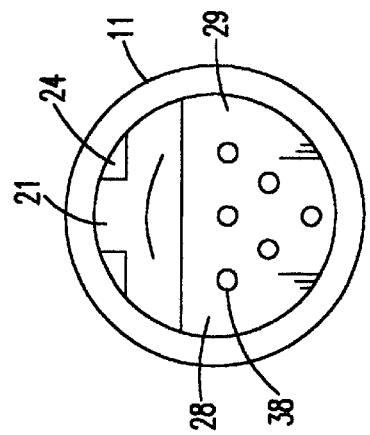
FIG. 7 is an end view according to another preferred embodiment of the present invention.
Figure 8:
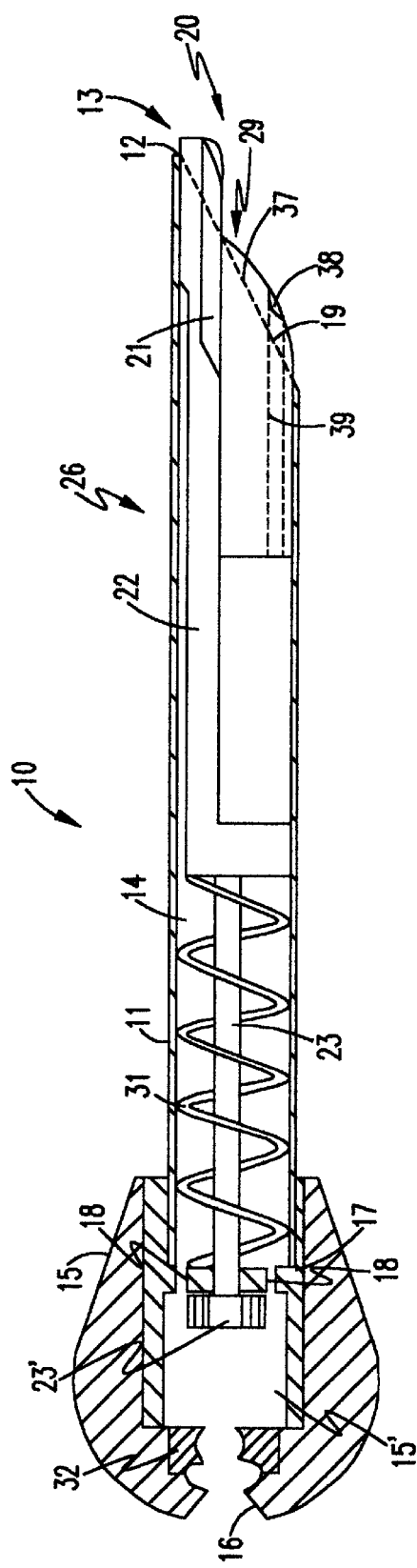
FIG. 8 is a cross-sectional view of the sleeve trocar according to another preferred embodiment thereof.
Figure 9:
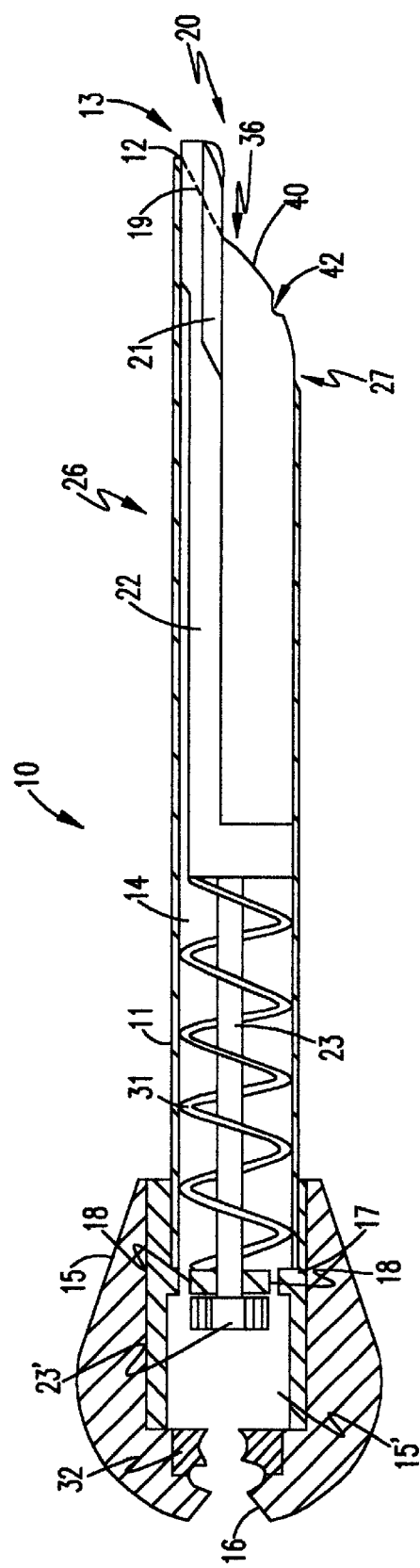
FIG. 9 is a cross-sectional view of the sleeve trocar according to another preferred embodiment of the present invention.

Other versions of the stationary obturator portion 27 are seen in FIGS. 7 and 8. In FIGS. 7 and 8, the stationary obturator portion 27 is formed with an optional opening 38 and throughbore 39 formed to allow gas to pass into the interior bore 14 of the sleeve member 11. Even if some tissue capture were to occur, at least some of the openings 38 should remain clear enough to activate the penetration indicator 32. As seen in FIG. 8, the second obturator portion 27 may be integrally formed with the sleeve member 11 to define an integrally formed face 40 projecting beyond the cutting edge 19. An optional opening 42 is provided to allow gas to pass therethrough from the internal body cavity.

Turning now to FIG. 10, another preferred embodiment of the invention is illustrated generally at 50. This embodiment includes two conical fixed obturator portions 54, 56 that are formed for insertion in the bore 14 of the sleeve member 11. The stationary obturator portions 54, 56 remain fixed within the sleeve member 11. A passage 57 is formed intermediate the first stationary obturator member 54 and the second stationary obturator 56. The endmost portion of the two obturator members 54, 56 project outwardly away from the sleeve member 11 in a conical manner to define a cutting area and aperture-forming region.

A moveable obturator 52 is formed as a generally sharpened rod member projecting through the passage 57 and fixed to a thrust member 51. The moveable obturator 52 includes a tapered and beveled tip as seen in FIG. 11 and illustrated generally at 60.

A surgical cutting edge 58 is formed on the outermost extent of the first stationary obturator portion 54 as seen in FIGS. 10 and 12. Also seen in FIG. 12, openings 62 are provided in the moveable obturator 52 for passage therethrough of insufflation gas to activate the penetration indicator 32.

Another preferred embodiment of the present invention is illustrated generally at 70 in FIGS. 13 and 15. As seen best in FIG. 15, this preferred embodiment 70 includes a three-portion fixed obturator and a three-portion moveable obturator. Returning now to FIG. 13, first and second stationary obturator portions are illustrated at 72 and 74 and project outwardly in a conical manner with a remaining portion of each stationary obturator member 72, 74, 76 extending into the bore formed in the sleeve member 11. A moveable obturator body 80 extends intermediate the stationary obturator portions 72, 74, 76 and includes three extending portions 84, 86, 88 as seen in FIG. 15. Cutting edge portions 90, 92, 94 project outwardly from the stationary obturator portion 72, 74, 76 to provide the cutting action of the present trocar. As seen in FIG. 15, the cutting edges 90, 92, 94 are spaced at 120° intervals around the full circle of the aperture-forming area. As seen in FIGS. 13 and 14, only a single moveable obturator portion is illustrated for clarity.

Gas ports 96 are formed in the moveable obturator portions 84, 86, 88 adjacent the cutting edge portions 92 and extend through the moveable obturator portion to be in fluid communication with the bore 14 formed in the sleeve member 11.

In operation, and with reference to the first preferred embodiment, a surgeon or other user grasps the handle 15 and commences the puncturing or piercing step by inserting the trocar 10 of the present invention into a body cavity wall using the sharp piercing tip 12. Abutment of the obturator head 25 with the body cavity wall forces the first obturator portion 26 rearwardly against the spring 31 which moves the blunt head 25 inwardly into the internal bore 14 of the sleeve member exposing the piercing tip 12. The cap 23' on the end of the shaft 23 working within the handle cavity 15 would act to limit travel of the first obturator portion 26. During the piercing step, the second obturator portion 27 would present the contour face 29 to the body cavity wall. Since, as has been determined, only the outermost extent of the cutting edge 19, including the piercing tip 12, actually does the cutting, blockage of the cutting edge 19 by the face 29 of the second obturator portion 27 is of no consequence in forming and defining the aperture in the body cavity wall.

Upon piercing the body cavity wall, the internal gas by which the body cavity has been insufflated escapes into the passageways 24, 24' prime and into the internal bore 14 of the sleeve member 11. This gas filling the internal bore 14 displaces any air that was in the internal channel through the flow passageways 18 in the insert member 17 and outwardly through the vent aperture 16 and the penetration indicator 32 giving an audible, whistling sound indicating that the body cavity has been breached. The gas flow, and consequently the audible sound, can be stopped by the surgeon pressing his hand over the vent aperture 16.

Simultaneously with the aforesaid gas flow, the bias on the first obturator portion 26 is no longer opposed by the abutment of the blunt tip 25 with the body cavity wall and, consequently, the spring 31 acts to bias the first obturator portion head 21 outwardly beyond the piercing tip 12, thereby preventing any contact of the piercing tip 12 with internal organs and saving such organs from damage by the piercing tip 12.

The present invention, by reducing the size of the moveable portion of the obturator assembly 20 reduces the amount of tissue which may be acquired by movement of the obturator inwardly relative to the cutting edge 19. Since the essential cutting is conducted by the piercing tip 12 and the edge 19 immediately adjacent thereto, the second non-moveable obturator portion does not interfere with cutting yet prevents substantial acquisition of tissue intermediate the second obturator portion 27 and the sleeve member 11. Further, due to the reduced transient weight provided by the two-portion obturator of the present invention, the moveable portion of the obturator assembly 20 travels faster than would the entire assembly 20 and, thereby, acts to more rapidly protect internal organs from the piercing tip 12.

It will therefore be readily understood by those persons skilled in the art that the present invention is susceptible of a broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

We claim:

1. A sleeve trocar for piercing tissue to provide a conduit to an internal body cavity insufflated by gas, said trocar comprising:

a sleeve member having a generally tubular wall member defining a bore therethrough;

a cutting edge;

an obturator assembly telescopically disposed within said sleeve member, said obturator assembly including at least one movable obturator portion having a generally blunt tip, said at least one movable obturator portion being movable between a first position wherein said generally blunt tip projects beyond said wall member and a second position wherein said generally blunt tip is disposed interiorly of at least a portion of said cutting edge, and at least one stationary obturator portion having a face member, said least one stationary obturator portion being fixed relative to said sleeve member with said face member projecting beyond a portion of said wall member; and means for biasing said at least one movable obturator portion into said first position;

wherein said cutting edge includes a sharp piercing tip formed thereon and said movable obturator portion projects beyond said piercing tip in said first position.

2. A sleeve trocar for piercing tissue to provide a conduit to an internal body cavity insufflated by gas, said trocar comprising:

a sleeve member having a generally tubular wall member defining a bore therethrough;

a cutting edge;

an obturator assembly telescopically disposed within said sleeve member, said obturator assembly including at least one movable obturator portion having a generally blunt tip, said at least one movable obturator portion being movable between a first position wherein said generally blunt tip projects beyond said wall member and a second position wherein said generally blunt tip is disposed interiorly of at least a portion of said cutting edge, and at least one stationary obturator portion having a face member, said least one stationary obturator portion being fixed relative to said sleeve member with said face member projecting beyond a portion of said wall member;

means for biasing said at least one movable obturator portion into said first position; and a penetration indication assembly including a penetration indicator operatively associated with said sleeve member and at least one passageway formed in said obturator assembly in fluid communication with said penetration indicator to allow gas to flow from a pierced body cavity through said at least one passageway to actuate said penetration indicator.

3. A sleeve trocar according to claim 2 wherein said penetration indicator produces an audible signal responsive to gas from said body cavity passing therethrough to thereby indicate that a body cavity wall has been breached.

4. A sleeve trocar according to claim 3 and further comprising a handle formed on one end of said sleeve member and having a bore extending therethrough to form said penetration indicator, said bore being in fluid communication with said at least one passageway and configured to produce an audible signal responsive to gas from said body cavity passing therethrough to thereby indicate that a body cavity wall has been breached.

5. A sleeve trocar according to claim 2 wherein said penetration indication assembly includes a plurality of passageways formed about a periphery of said at least one movable obturator portion to form peripheral passageways, said peripheral passageways being formed by a combination of said tubular wall of said sleeve member and walls formed in said periphery of said at least one movable obturator portion.

6. A sleeve trocar according to claim 2 wherein said penetration indication assembly includes a plurality of passageways formed about a periphery of said least one stationary obturator portion to form peripheral passageways, said peripheral passageways being formed by a combination of said tubular wall of said sleeve member and walls formed in said periphery of said least one stationary obturator portion.

7. A sleeve trocar according to claim 2 wherein said penetration indication assembly includes a plurality of passageways formed about respective peripheries of said at least one movable obturator portion and said least one stationary obturator portion to form peripheral passageways, said peripheral passageways being formed by a combination of said tubular wall of said sleeve member and walls formed in said respective peripheries of said at least one movable obturator portion and said least one stationary obturator portion.

8. A sleeve trocar according to claim 2 wherein said plurality of passageways are formed as throughbores in said face member to extend through said face member and said stationary obturator portion in fluid communication with said bore formed in said sleeve member and said bore formed in said handle.

9. A sleeve trocar for piercing tissue to provide a conduit to an internal body cavity insufflated by gas, said trocar comprising:

a sleeve member having a generally tubular wall member defining a bore through said sleeve member;

an obturator assembly telescopically disposed within said sleeve member, said obturator assembly including at least one movable obturator portion having a generally blunt tip, said at least one movable obturator portion being movable between a first position wherein said generally blunt tip projects beyond said wall member and a second position wherein said generally blunt tip is disposed within said bore, and at least one stationary obturator portion having a face, said least one stationary obturator portion being formed as a plug member and fixed relative to said sleeve member with said face being formed on one end of said plug member with said face projecting beyond a portion of said wall member;

a spring disposed within said tubular sleeve member, said spring being fixed at one end to said at least one movable obturator portion with the other end fixed to a stop member formed within said sleeve member for biasing said at least one movable obturator portion outwardly beyond said wall member; and a penetration indication assembly including a penetration indicator operatively associated with said sleeve member for producing an audible signal responsive to gas from said body cavity passing therethrough and at least one passageway formed in said obturator assembly in fluid communication with said penetration indicator to allow gas to flow from a pierced body cavity through said at least one passageway to actuate said penetration indicator to thereby indicate that a body cavity wall has been breached.

10. A sleeve trocar according to claim 9 wherein said sleeve member includes a cutting edge with a sharp piercing tip formed thereon and said movable obturator portion projects beyond said piercing tip in said first position.

11. A sleeve trocar according to claim 9 wherein said face member includes a smoothly contoured surface for smooth separation of tissue for enhanced ease of entry of said trocar into the body cavity.

12. A sleeve trocar according to claim 9 and further comprising a handle formed on one end of said sleeve member and having a bore formed therethrough to form said penetration indicator, said bore being in fluid communication with said at least one passageway and configured to produce an audible signal responsive to gas from said body cavity passing therethrough to thereby indicate that a body cavity wall has been breached.

13. A sleeve trocar according to claim 9 wherein said penetration indication assembly includes a plurality of passageways formed about a periphery of said at least one movable obturator portion to form peripheral passageways, said peripheral passageways being formed by a combination of said tubular wall of said sleeve member and walls formed in said periphery of said at least one movable obturator portion.

14. A sleeve trocar according to claim 9 wherein said penetration indication assembly includes a plurality of passageways formed about a periphery of said least one stationary obturator portion to form peripheral passageways, said peripheral passageways being formed by a combination of said tubular wall of said sleeve member and walls formed in said periphery of said least one stationary obturator portion.

15. A sleeve trocar according to claim 9 wherein said penetration indication assembly includes a plurality of passageways formed about respective peripheries of said at least one movable obturator portion and said least one stationary obturator portion to form peripheral passageways, said peripheral passageways being formed by a combination of said tubular wall of said sleeve member and walls formed in said respective peripheries of said at least one movable obturator portion and said least one stationary obturator portion.

16. A sleeve trocar according to claim 9 wherein said plurality of passageways are formed as throughbores in said face member to extend through said face member and said stationary obturator portion in fluid communication with said bore in said sleeve member and said bore in said handle.

17. A sleeve trocar for piercing tissue to provide a conduit to an internal body cavity insufflated by gas, said trocar comprising:
  a sleeve member having a generally tubular wall member defining a bore through said sleeve member, a first end portion formed with a beveled cutting edge having a piercing tip formed thereon, and defining an aperture region for forming and defining an aperture in body cavity walls; and an opposing second end portion;
  an obturator assembly telescopically disposed within said sleeve member, said obturator assembly including an obturator head having a generally blunt tip, said obturator head being movable between a first position wherein said generally blunt tip projects beyond said piercing tip and a second position wherein said generally blunt tip is disposed within said bore, said obturator head being sized to occupy a predetermined portion of said aperture region leaving a remainder of said aperture region;
  means for biasing said obturator head into said first position; and
  an obturation face member fixed relative to said sleeve member with a portion of said obturation face member projecting beyond a portion of said cutting edge, said obturation face member being sized to occupy said remainder of said aperture region.

18. A sleeve trocar according to claim 17 wherein said obturator head is sized to occupy less than half of said aperture region.

19. A sleeve trocar according to claim 17 wherein said obturation face member includes a plug member fixedly disposed within said sleeve member with a face projection being formed on one end of said plug member and sized to project beyond a portion of said beveled cutting edge.

20. A sleeve trocar according to claim 19 wherein said face projection includes a smoothly contoured surface for smooth separation of tissue for enhanced ease of entry of said trocar into the body cavity.

21. A sleeve trocar according to claim 17 wherein said obturation face member is formed integrally with said sleeve member with a face projection sized to project beyond a portion of said beveled cutting edge.

22. A sleeve trocar according to claim 21 wherein said face projection includes a smoothly contoured surface for smooth separation of tissue for enhanced ease of entry of said trocar into the body cavity.

23. A sleeve trocar according to claim 17 and further comprising a penetration indication assembly including a penetration indicator operatively associated with said sleeve member and at least one passageway formed in said obturator head in fluid communication with said penetration indicator to allow gas to flow from a pierced body cavity through said at least one passageway to actuate said penetration indicator.

24. A sleeve trocar according to claim 23 wherein said penetration indicator produces an audible signal responsive to gas from said body cavity passing therethrough to thereby indicate that a body cavity wall has been breached.

25. A sleeve trocar according to claim 24 and further comprising a handle formed on said opposing end of said sleeve member and said penetration indicator is formed as bore extending through handle in fluid communication with said at least one passageway and configured to produce an audible signal responsive to gas from said body cavity passing therethrough to thereby indicate that a body cavity wall has been breached.

26. A sleeve trocar according to claim 23 wherein said penetration indication assembly includes a plurality of passageways formed about a periphery of said obturator head to form peripheral passageways, said peripheral passageways being formed by a combination of said tubular wall of said sleeve member and walls formed in said periphery of said obturator head.

27. A sleeve trocar according to claim 23 wherein said penetration indication assembly includes a plurality of passageways formed about a periphery of said obturation face member to form peripheral passageways, said peripheral passageways being formed by a combination of said tubular wall of said sleeve member and walls formed in said periphery of said obturation face member.

28. A sleeve trocar according to claim 23 wherein said penetration indication assembly includes a plurality of passageways formed about respective peripheries of said obturator head and said obturation face member to form peripheral passageways, said peripheral passageways being formed by a combination of said tubular wall of said sleeve member and walls formed in said respective peripheries of said obturator head and said obturation face member.

29. A sleeve trocar according to claim 17 wherein said plurality of passageways are formed as throughbores in said face member to extend through said face member and said stationary obturator portion in fluid communication with said bore formed in said sleeve member and said bore formed in said handle.

30. A sleeve trocar according to claim 17 wherein said means for biasing said obturator head into said first position includes a spring disposed within said tubular sleeve member, said spring being fixed at one end to said obturator head with the other end fixed within said sleeve member for biasing said obturator head outwardly beyond said piercing tip.

31. A sleeve trocar for piercing tissue to provide a conduit to an internal body cavity insufflated by gas, said trocar comprising:
  a sleeve member having a generally tubular wall member defining a bore therethrough;
  a cutting edge;
  an obturator assembly telescopically disposed within said sleeve member, said obturator assembly including at least one movable obturator portion having a generally blunt tip, said at least one movable obturator portion being movable between a first position wherein said generally blunt tip projects beyond said wall member and a second position wherein said generally blunt tip is disposed interiorly of at least a portion of said cutting edge, and at least one stationary obturator portion having a face member, said least one stationary obturator portion being fixed relative to said sleeve member with said face member protecting beyond a portion of said wall member; and
  means for biasing said at least one movable obturator portion into said first position;
  wherein said obturator assembly includes a conical stationary obturator portion fixed in said sleeve member and projecting outwardly therefrom, said conical stationary obturator portion being formed from at least two stationary obturator members in abutment with one another, extending a predetermined distance into said bore formed in said sleeve member and having a obturator passage formed therebetween with said movable obturator portion being disposed in said obturator passage for movement between said first and second positions.

32. A sleeve trocar according to claim 31 and further comprising a cutting edge formed on at least one of said stationary obturator members adjacent said passage in which said movable obturator is disposed.

33. A sleeve trocar according to claim 31 and further comprising a penetration indication assembly including a penetration indicator operatively associated with said sleeve member and at least one passageway formed in said obturator assembly in fluid communication with said penetration indicator to allow gas to flow from a pierced body cavity through said at least one passageway to actuate said penetration indicator.

34. A sleeve trocar according to claim 33 wherein said movable obturator portion includes said at least one passageway formed therein as at least one throughbore formed in fluid communication with said penetration indicator to allow gas to flow from a pierced body cavity through said at least one passageway to actuate said penetration indicator.

35. A sleeve trocar for piercing tissue to provide a conduit to an internal body cavity insufflated by gas, said trocar comprising:

a sleeve member having a generally tubular wall member defining a bore therethrough;

a cutting edge;

an obturator assembly telescopically disposed within said sleeve member, said obturator assembly including at least one movable obturator portion having a generally blunt tip, said at least one movable obturator portion being movable between a first position wherein said generally blunt tip projects beyond said wall member and a second position wherein said generally blunt tip is disposed interiorly of at least a portion of said cutting edge, and at least one stationary obturator portion having a face member, said least one stationary obturator portion being fixed relative to said sleeve member with said face member projecting beyond a portion of said wall member; and means for biasing said at least one movable obturator portion into said first position;

wherein said obturator assembly includes a conical stationary obturator portion fixed in said sleeve member and projecting outwardly therefrom, said conical stationary obturator portion being formed from at least three obturator members in abutment with one another, extending a predetermined distance into said bore and having three obturator passages formed therebetween with said movable obturator portion being formed as three movable obturator members disposed in respective said obturator passages for movement between said first and second positions.

36. A sleeve trocar according to claim 35 and further comprising at least one cutting edge formed on at least one of said stationary obturator members adjacent at least one said passage in which said movable obturator is disposed.

37. A sleeve trocar according to claim 35 and further comprising a penetration indication assembly including a penetration indicator operatively associated with said sleeve member and at least one passageway formed in said obturator assembly in fluid communication with said penetration indicator to allow gas to flow from a pierced body cavity through said at least one passageway to actuate said penetration indicator.

38. A sleeve trocar according to claim 37 wherein said movable obturator portion includes said at least one passageway formed therein as at least one throughbore formed in fluid communication with said penetration indicator to allow gas to flow from a pierced body cavity through said at least one passageway to actuate said penetration indicator.

39. A sleeve trocar for piercing tissue to provide a conduit to an internal body cavity insufflated by gas, said trocar comprising:

a sleeve member having a generally tubular wall member defining a bore through said sleeve member;

an obturator assembly telescopically disposed within said sleeve member, said obturator assembly including a conical stationary obturator portion fixed in said sleeve member and projecting outwardly therefrom, at least one movable obturator portion having a generally blunt tip, said at least one movable obturator portion being movable between a first position wherein said generally blunt tip projects beyond said wall member and a second position wherein said generally blunt tip is disposed within said conical stationary obturator portion, wherein said conical stationary obturator portion being formed from at least two obturator members in abutment with one another, extending a predetermined distance into said passageway and having a obturator passage formed therebetween with said movable obturator portion being disposed in said obturator passage for movement between said first and second positions, said conical stationary obturator portion having a face member, said conical stationary obturator portion being formed as a two plug members, said face member being formed on one end of said plug member with said face projecting beyond a portion of said wall member;

a cutting edge formed on at least one of said stationary obturator members adjacent said passage in which said movable obturator is disposed;

a spring disposed within said tubular sleeve member, said spring being fixed at one end to said at least one movable obturator portion with the other end fixed to a stop member formed within said sleeve member for biasing said at least one movable obturator portion outwardly beyond said wall member; and a penetration indication assembly including a penetration indicator operatively associated with said sleeve member for producing an audible signal responsive to gas from said body cavity passing therethrough and at least one passageway formed in said obturator assembly in fluid communication with said penetration indicator to allow gas to flow from a pierced body cavity through said at least one passageway to actuate said penetration indicator to thereby indicate that a body cavity wall has been breached.

40. A sleeve trocar according to claim 39 and further comprising a penetration indication assembly including a penetration indicator operatively associated with said sleeve member and at least one passageway formed in said obturator assembly in fluid communication with said penetration indicator to allow gas to flow from a pierced body cavity through said at least one passageway to actuate said penetration indicator.

41. A sleeve trocar according to claim 39 wherein said movable obturator portion includes said at least one passageway formed therein as at least one throughbore formed in fluid communication with said penetration indicator to allow gas to flow from a pierced body cavity through said at least one passageway to actuate said penetration indicator.

42. A sleeve trocar according to claim 39 and further comprising a handle formed on one end of said sleeve member and having a bore formed therethrough to form said penetration indicator, said bore being in fluid communication with said at least one passageway and configured to produce an audible signal responsive to gas from said body cavity passing therethrough to thereby indicate that a body cavity wall has been breached.

43. A sleeve trocar according to claim 39 wherein said penetration indication assembly includes a plurality of passageways formed about a periphery of said at least one movable obturator portion to form peripheral passageways, said peripheral passageways being formed by a combination of said tubular wall of said sleeve member and walls formed in said periphery of said at least one movable obturator portion.

44. A sleeve trocar according to claim 39 wherein said penetration indication assembly includes a plurality of passageways formed about a periphery of said least one stationary obturator portion to form peripheral passageways, said peripheral passageways being formed by a combination of said tubular wall of said sleeve member and walls formed in said periphery of said least one stationary obturator portion.

45. A sleeve trocar according to claim 39 wherein said penetration indication assembly includes a plurality of passageways formed about respective peripheries of said at least one movable obturator portion and said least one stationary obturator portion to form peripheral passageways, said peripheral passageways being formed by a combination of said tubular wall of said sleeve member and walls formed in said respective peripheries of said at least one movable obturator portion and said least one stationary obturator portion.

46. A sleeve trocar according to claim 39 wherein said plurality of passageways are formed as throughbores in said face member to extend through said face member and said stationary obturator portion in fluid communication with said bore in said sleeve member and said bore in said handle.

47. A sleeve trocar for piercing tissue to provide a conduit to an internal body cavity insufflated by gas, said trocar comprising:

a sleeve member having a generally tubular wall member defining a bore through said sleeve member;

an obturator assembly telescopically disposed within said sleeve member, said obturator assembly including a cutting edge, at least one movable obturator portion having a generally blunt tip, said at least one movable obturator portion being movable between a first position wherein said generally blunt tip projects beyond said wall member and a second position wherein said generally blunt tip is disposed interiorly of said cutting edge, and a conical stationary obturator portion fixed in said sleeve member and projecting outwardly therefrom, said conical stationary obturator portion being formed from at least three obturator members in abutment with one another, extending a predetermined distance into said passageway and having three obturator passages formed therebetween with said movable obturator portion being formed as three movable obturator members disposed in said obturator passage for movement between said first and second positions, said conical stationary obturator portion having a face member, said face member being formed on one end of said conical stationary obturator portion with said face member projecting beyond a portion of said wall member; said cutting edge formed on at least one of said stationary obturator members adjacent at least one of said passages in which said movable obturator is disposed;

a spring disposed within said tubular sleeve member, said spring being fixed at one end to said at least one movable obturator portion with the other end fixed to a stop member formed within said sleeve member for biasing said at least one movable obturator portion outwardly beyond said wall member; and a penetration indication assembly including a penetration indicator operatively associated with said sleeve member for producing an audible signal responsive to gas from said body cavity passing therethrough and at least one passageway formed in said obturator assembly in fluid communication with said penetration indicator to allow gas to flow from a pierced body cavity through said at least one passageway to actuate said penetration indicator to thereby indicate that a body cavity wall has been breached.

48. A sleeve trocar according to claim 47 wherein said movable obturator portion includes said at least one passageway formed therein as at least one throughbore formed in fluid communication with said penetration indicator to allow gas to flow from a pierced body cavity through said at least one passageway to actuate said penetration indicator.

49. A sleeve trocar according to claim 47 wherein said face member includes a smoothly contoured surface for smooth separation of tissue for enhanced ease of entry of said trocar into the body cavity.

50. A sleeve trocar according to claim 47 and further comprising a handle formed on one end of said sleeve member and having a bore formed therethrough to form said penetration indicator, said bore being in fluid communication with said at least one passageway and configured to produce an audible signal responsive to gas from said body cavity passing therethrough to thereby indicate that a body cavity wall has been breached.

51. A sleeve trocar according to claim 47 wherein said penetration indication assembly includes a plurality of passageways formed about a periphery of said at least one movable obturator portion to form peripheral passageways, said peripheral passageways being formed by a combination of said tubular wall of said sleeve member and walls formed in said periphery of said at least one movable obturator portion.

52. A sleeve trocar according to claim 47 wherein said penetration indication assembly includes a plurality of passageways formed about a periphery of said least one stationary obturator portion to form peripheral passageways, said peripheral passageways being formed by a combination of said tubular wall of said sleeve member and walls formed in said periphery of said least one stationary obturator portion.

53. A sleeve trocar according to claim 47 wherein said penetration indication assembly includes a plurality of passageways formed about respective peripheries of said at least one movable obturator portion and said least one stationary obturator portion to form peripheral passageways, said peripheral passageways being formed by a combination of said tubular wall of said sleeve member and walls formed in said respective peripheries of said at least one movable obturator portion and said least one stationary obturator portion.

54. A sleeve trocar according to claim 47 wherein said plurality of passageways are formed as throughbores in said face member to extend through said face member and said stationary obturator portion in fluid communication with said bore in said sleeve member and said bore in said handle.

* * * * *